(12) United States Patent
Gradel

(10) Patent No.: US 11,026,703 B2
(45) Date of Patent: Jun. 8, 2021

(54) METHOD FOR THE PRODUCTION OF A REAMER

(71) Applicant: Deuxventorio Sàrl, Gland (CH)

(72) Inventor: Thomas Gradel, Marignier (FR)

(73) Assignee: Deuxventorio Sàrl, Gland (CH)

( * ) Notice: Subject to any disclaimer, the term of this patent is extended or adjusted under 35 U.S.C. 154(b) by 184 days.

(21) Appl. No.: 16/310,009

(22) PCT Filed: Jul. 11, 2017

(86) PCT No.: PCT/IB2017/054172
§ 371 (c)(1),
(2) Date: Dec. 14, 2018

(87) PCT Pub. No.: WO2018/011708
PCT Pub. Date: Jan. 18, 2018

(65) Prior Publication Data
US 2019/0167278 A1 Jun. 6, 2019

(30) Foreign Application Priority Data
Jul. 12, 2016 (FR) ..................... 16 56688

(51) Int. Cl.
| | |
|---|---|
| *A61B 17/16* | (2006.01) |
| *B21D 31/02* | (2006.01) |
| *B23C 5/00* | (2006.01) |
| *B23C 5/02* | (2006.01) |
| *A61B 17/00* | (2006.01) |

(52) U.S. Cl.
CPC ......... *A61B 17/1666* (2013.01); *B21D 31/02* (2013.01); *B23C 5/006* (2013.01); *B23C 5/02* (2013.01); *A61B 2017/00526* (2013.01); *A61B 2017/1602* (2013.01)

(58) Field of Classification Search
CPC A61B 17/1666; A61B 17/8863; B21D 31/02; B21D 28/24; B23P 15/46
See application file for complete search history.

(56) References Cited

U.S. PATENT DOCUMENTS

| | | | | |
|---|---|---|---|---|
| 4,182,204 | A * | 1/1980 | Coon | B23D 73/04 76/116 |
| 5,968,049 | A | 10/1999 | Da Rold | |
| 2003/0135219 | A1 | 7/2003 | Salyer | |
| 2003/0181916 | A1 | 9/2003 | Wolford | |
| 2005/0113837 | A1 | 5/2005 | Salyer | |
| 2006/0095041 | A1 | 5/2006 | Fehlbaum | |
| 2010/0069908 | A1* | 3/2010 | Sidebotham | A61B 17/1666 606/81 |
| 2013/0245628 | A1* | 9/2013 | Sidebotham | A61B 17/16 606/80 |
| 2014/0188116 | A1 | 7/2014 | Sidebotham | |
| 2017/0311958 | A1 | 11/2017 | Gradel | |

* cited by examiner

*Primary Examiner* — Andrew Yang
(74) *Attorney, Agent, or Firm* — William H. Eilberg

(57) ABSTRACT

A method for the production of a reamer, such as a burr for milling a patient's acetabular cavity, including a substantially hemispherical, hollow cutting body with a perforated wall. The method includes a step of forming at least one tooth by stamping the wall, during which an area of the thinned portion of the wall, adjacent to a hole, is pressed between a punch and an anvil.

7 Claims, 7 Drawing Sheets

METHOD FOR THE PRODUCTION OF A REAMER

TECHNICAL FIELD OF THE INVENTION

The present invention relates to a method for producing a reamer, such as a milling cutter intended to mill the acetabular cavity of a patient during a surgical hip operation.

A reamer, such as a milling cutter intended to mill the acetabular cavity of a patient, comprising a substantially hemispherical hollow cutter body with perforated wall, is known. To form a tooth on such a milling cutter, it is known from the document EP 0 879 577 A2 to proceed by means of the following three successive steps:
- in a first step, forming a hole in the wall of the cutter body to define the outlines of a tongue,
- in a second step, accurately forming, by milling, a reference edge, and accurately sharpening, by milling, a cutting edge on the free edge of said tongue;
- in a third step, raising the tongue with a precise angle through confinement of said tongue between a punch and an anvil, by provoking a folding in a zone situated away from the cutting edge.

Forming the cutting edge in a step prior to the raising of the tongue to have the cutting edge protrude relative to the wall of the cutter body makes the production method lengthy and costly. Furthermore, such a tooth formed by a folded tongue has a weak structural rigidity and has a tendency to be deformed when forces are applied by the surgeon. The cutting characteristics of such a milling cutter are not therefore reliable or durable over time.

The documents US 2014/188116 A1, WO 2016/071867 A1, US 2006/095041 A1 and US 2003/132213 A1, for their part, describe a production method comprising the following steps:
- drilling the wall of the cutter body in a drilling direction substantially at right angles to the wall,
- chamfering, by machining (by means of a drill or a milling cutter) the periphery of the hole obtained to form a cutting edge with acute profile,
- plastically deforming, by stamping, a portion of wall extending radially from, and away from the hole formed in the wall, to form the tooth.

The order of the steps of production of the chamfer by machining and of plastic deformation by stamping is sometimes reversed.

In such a method, the cutting edge is produced by machining (removal) of a part of the constituent matter of the wall at the periphery of the hole, which is lengthy and costly. The oblique face of the chamfer provides a gradual radial increase of thickness at the periphery of the hole, then the stamping operation makes it possible to have a part of this chamfer protruding relative to the substantially hemispherical outer surface of the hollow cutter body, to obtain a tooth which will cut the bony matter in the milling of the acetabular cavity of a patient during a surgical hip operation.

The chamfer does not however always make it possible to obtain adequate cutting capabilities such that a manual sharpening of the protruding chamfer part is often performed. This sharpening is done tooth by tooth and takes a long time. The production cost thus excludes the possibility of implementing a disposable reamer policy for the reduction in risks of infection in health establishments.

Furthermore, it is essential for the operator in charge of the sharpening to have a certain dexterity to obtain teeth with relatively uniform cutting characteristics. If the teeth do not have cutting characteristics that are sufficiently uniform, at the end of the sharpening thereof, forces that are unevenly distributed on the bone may occur in the milling of the acetabular cavity, resulting in vibrations that may give the acetabular cavity a cross section that is substantially polygonal (instead of being circular). The correct installation and bone integration of the cup in the acetabular cavity can then be compromised.

Finally, the teeth have a tendency to wear too rapidly. Thus, the cutting characteristics of the reamers diminish fairly quickly (even too quickly) in time. That compromises the possibility of re-using a reamer multiple times in order to amortize the acquisition costs thereof.

It should be noted that, in the documents US 2014/188116 A1, WO 2016/071867 A1, US 2006/095041 A1 and US 2003/0135219 A1, practically only a punch is used. Nowhere is the use of an anvil against which a pressing can be performed explained.

The documents US 2003/0181916 and US 2005/0113837 A1 describe a production method according to the preamble of claim 1. The edge of the hole undergoes no sharpening prior to or after the stamping forming the protruding tooth on the wall of the cutter body. The production method of the documents 2003/0181916 and US 2005/0113837 A1 is thus less costly. However, the reliability and the durability over time of the cutting characteristics of the teeth are relatively unsatisfactory. The cutting characteristics of the teeth are in fact rather variable from one tooth to another, and they quickly tend to deteriorate over time, particularly after several uses of the reamer.

SUMMARY OF THE INVENTION

One problem set out by the present invention is to propose a rapid and inexpensive method for producing a reamer, such as a milling cutter intended to mill the acetabular cavity of a patient.

At the same time, the present invention, aims to provide a production method that can easily be automated and that makes it possible to obtain cutting characteristics that are more reliable and more durable over time, even after several uses.

To achieve these objects, and others, the invention proposes a method for producing a reamer such as a milling cutter intended to mill the acetabular cavity of a patient and comprising a substantially hemispherical hollow cutter body with perforated wall, said method comprising a step in which at least one tooth is formed by stamping the wall by means of a punch plastically deforming a portion of wall extending radially from and away from, a hole formed in the wall; according to the invention, in the stamping of the tooth, a zone of the deformed portion of wall, adjacent to the hole, is thinned and pressed by the punch against an anvil.

The stamping and the subsequent pressing between the punch and the anvil of the zone of the deformed wall portion provide a thinning of the wall that is drawn to form the protruding tooth on the wall of the cutter body. This thinning provides cutting capabilities at the free edge of the duly formed tooth. By suitably controlling the pressing force, a thinning is achieved that is better controlled and reproducible for more uniform cutting characteristics between all the teeth.

This thinning is not done by removal of material but by drawing, then by stressing and creep in pinching. The cutting edge is thus formed in the stamping. In the pressing (or pinching), there then occurs a kind of local cold working of the tooth (or a fiber orientation of the material) which gives an increased structural strength and a better durability in time during the re-use of the reamer.

The forming of the tooth can easily be automated, is rapid, and can be implemented easily in a follow-on tool for example. The cost of production of the reamer is thus greatly reduced.

Preferably, provision can be made for:
the punch to comprise a free end with set pressing surface, in the step of forming of the tooth, the generatrix of the pressing surface to be oblique relative to the plane defined by the orifice of the hole.

Such a punch is relatively simple and inexpensive to produce.

Preferably, provision can be made for:
the anvil to comprise a set pressing surface whose generatrix is oblique relative to the plane defined by the orifice of the hole,
in the forming of the tooth, the angle between the generatrix of the pressing surface of the anvil and the plane defined by the orifice of the hole to be smaller than the angle between the generatrix of the pressing surface of the punch and the plane defined by the orifice of the hole.

This difference in angle makes it possible to obtain a good gradual thinning with a strong cola working or fiber orientation of the material in the vicinity of the free edge of the tooth (intended to form the cutting edge of the tooth). On the other hand, a greater thickness of material is retained by moving away from the cutting edge and from the hole, which gives the tooth a good structural rigidity. In practice, the difference in angle can preferably be approximately 2 degrees.

Advantageously, provision can be made, until the step of forming of the tooth, for the cutter body to take the form of a perforated flat metal blank. It is thus possible to form several teeth simultaneously through the use of multiple mutually parallel punches.

Advantageously, the flat metal blank can have a thickness of between approximately 0.4 mm and approximately 1 mm.

Preferably, after the forming of the tooth, the flat blank can be cut to obtain a plurality of perforated and toothed petals extending radially from, a central zone from which the petals extend to a free end, and separated from one another by radial lateral spaces.

Advantageously, after the cutting of the flat blank to form the petals, it is possible to:
shape the flat blank as a hemisphere,
add and fix the free ends of the petals onto an at least partially circular base body.

Advantageously, the cutter body can be made of stainless steel, preferably of 304 L or 316 L grade stainless steel.

BRIEF DESCRIPTION OF THE DRAWINGS

Other objects, features and advantages of the present invention will emerge from the following description of particular embodiments, given in relation to the attached figures, in which.

DESCRIPTION OF PREFERRED EMBODIMENTS

Figure 1:
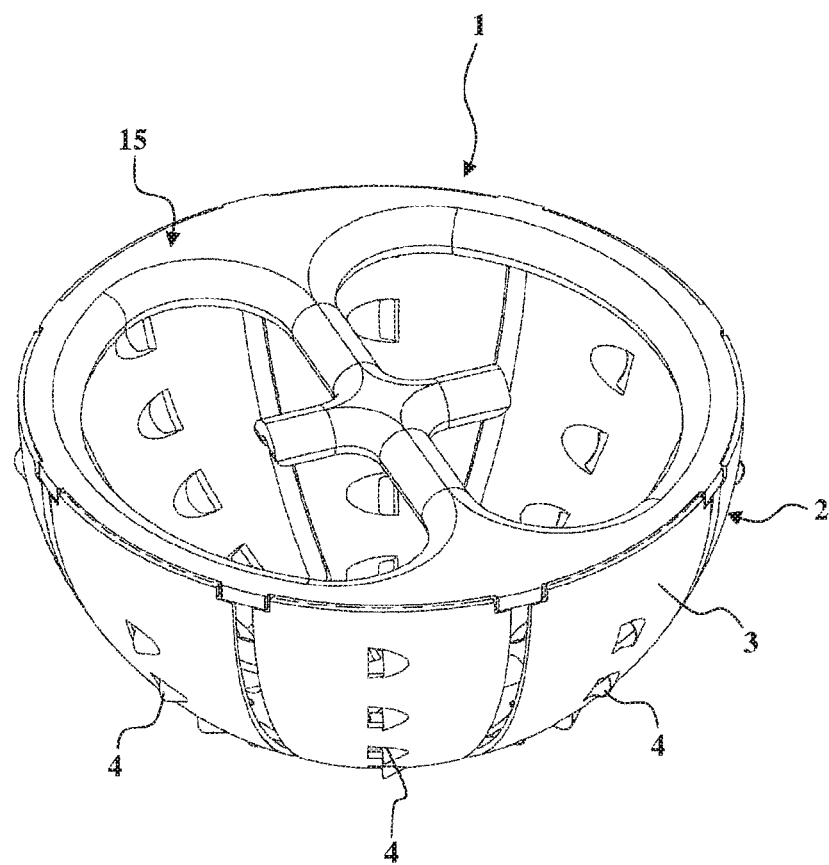
FIG. 1 is a perspective view of an exemplary embodiment of a reamer according to the invention.

FIG. 1 illustrates a reamer 1 which is a milling cutter intended to mill the acetabular cavity of a patient. The reamer 1 comprises a substantially hemispherical hollow cutter body 2 with perforated wall 3. A plurality of teeth 4 have been formed by deformation of the wall 3. Their forming is more particularly done by stamping in a follow-on tool, as will be explained hereinbelow using FIGS. 2 to 12.

Figure 3:
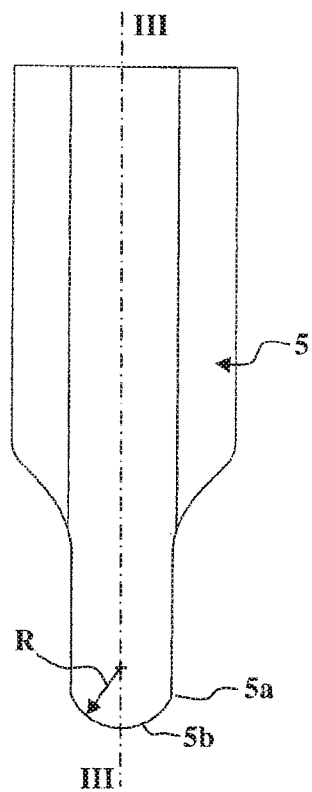
FIG. 3 is a front view of a punch.
Figure 4:
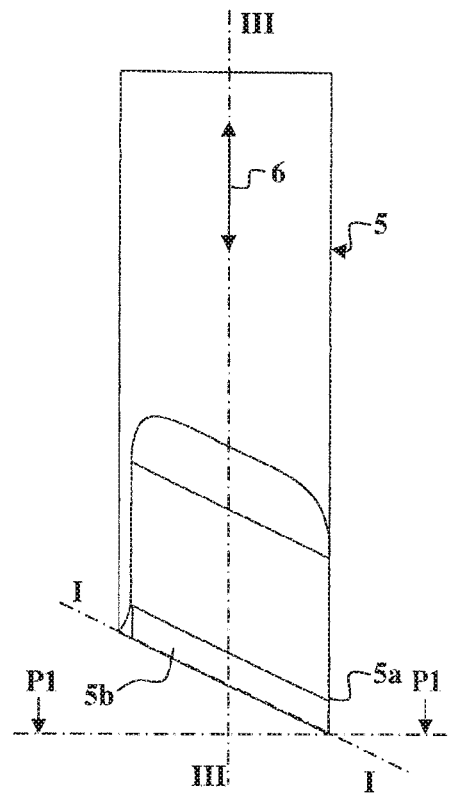
FIG. 4 is a side view of the punch of FIG. 3.
Figure 5:
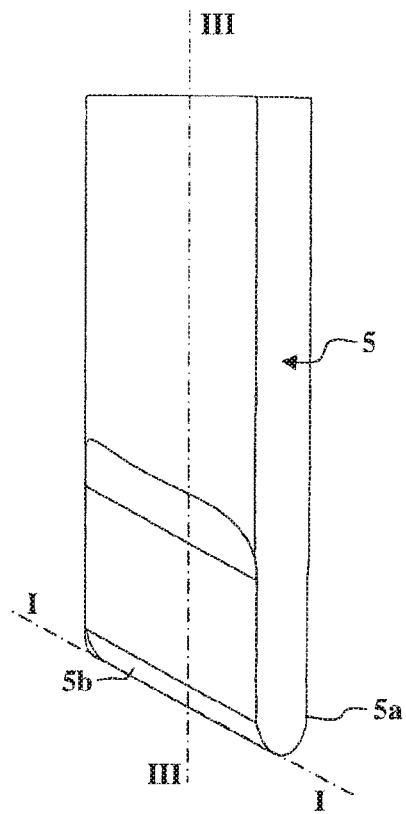
FIG. 5 is a perspective view of the punch of FIG. 3.

In said stamping, use is made of a punch 5 as illustrated in FIGS. 3 to 5. The punch 5 comprises a free end 5a with set pressing surface 5b whose cross section is in the form of a circular arc of radius R (FIG. 3). The punch 5 is intended to be driven by a two-way translational movement in the axial direction III-III illustrated by the double arrow 5 while a wall 3 to be deformed is located in the plane P1 illustrated in FIG. 6. Thus, in the step of forming of a tooth 4, the generatrix I-I of the pressing surface 5b is oblique relative to the plane P1 (FIG. 9).

Figure 2:
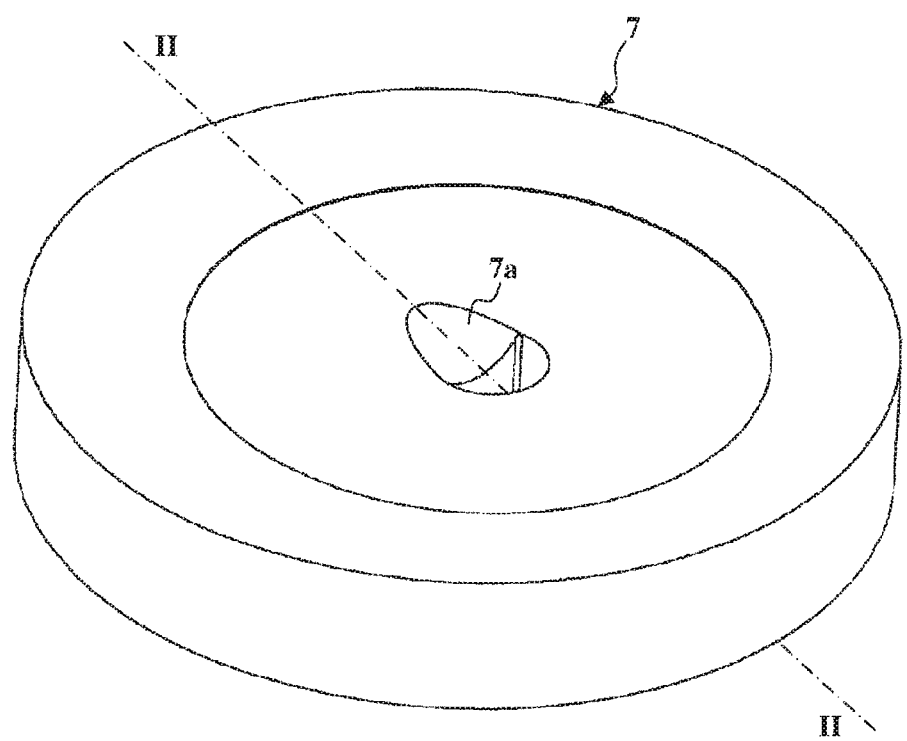
FIG. 2 is a perspective view of a follow-on tool workstation.

In said stamping, users simultaneously made of an anvil 7 as illustrated in FIG. 2. The anvil 7 comprises a set pressing surface 7a that also has a cross section in the form of a circular arc of radius slightly greater than the radius R. As is more particularly visible in FIG. 6, the generatrix II-II of the pressing surface 7a of the anvil 7 is oblique relative to the plane P1 in which the face of the wall 3 which is not in contact with the anvil 7 is located. More specifically, the plane P1 is defined by the orifice 9 of the hole 10 formed in the wall 3.

The pressing surfaces 5b and 7a can have a cross section of different form. It is for example possible to envisage a cross section composed of the succession of three circular arcs of different radii, in particular with the first and third radii equal and smaller than the second radius. The pressing surface 5b then has a vertex (while the pressing surface 7a has a bottom) that is a little flattened.

Figure 9:
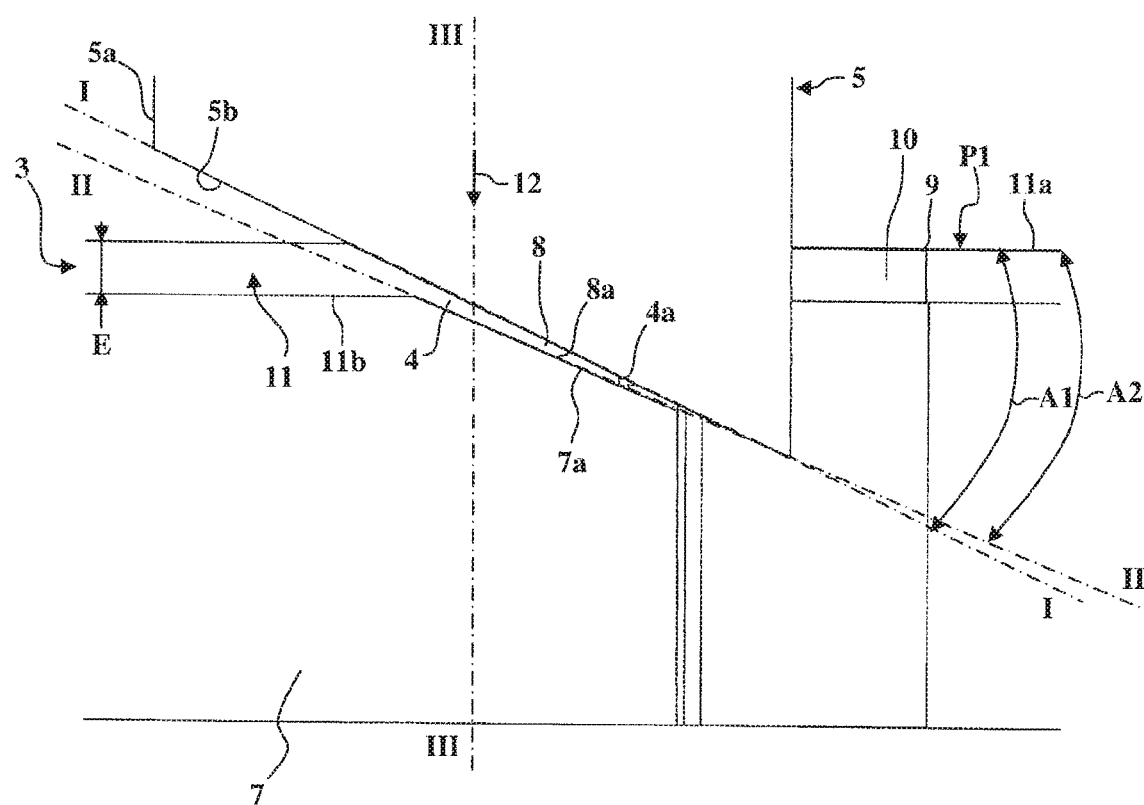
FIG. 9 is a detailed and side view of FIG. 8.
Figure 10:
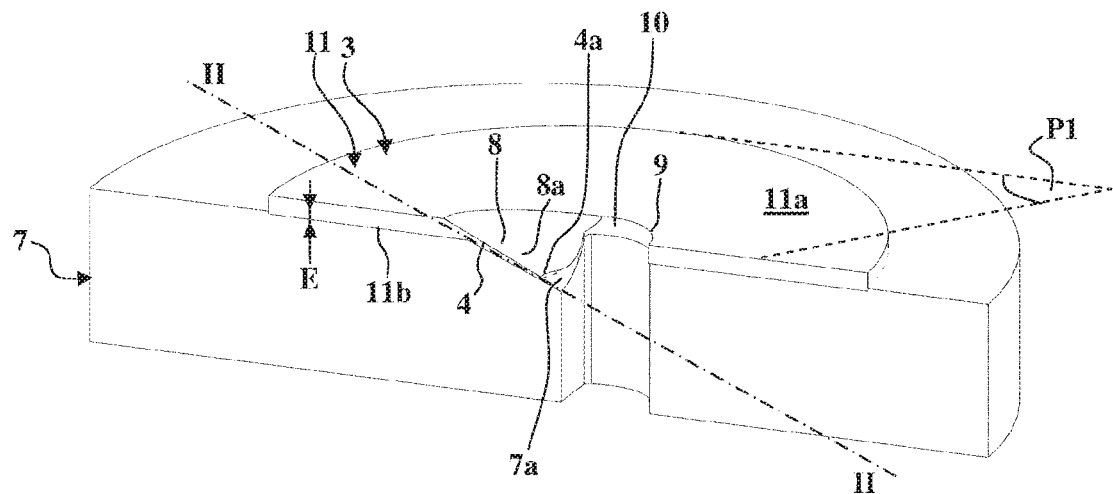
FIG. 10 is a perspective and cross-sectional view of the workstation of FIG. 2 after the stamping of the metal blank to form a tooth.

In the detailed view of FIG. 9 more specifically illustrating the cooperation between the punch 5 and the anvil 7 in the forming of a tooth 4, it can be seen that the angle A2 between the generatrix II-II of the pressing surface 7a of the anvil 7 and the plane P1 is smaller than the angle A1 between the generatrix I-I of the pressing surface 5b of the punch 5 and the plane P1. This difference is approximately 2 degrees.

Figure 6:
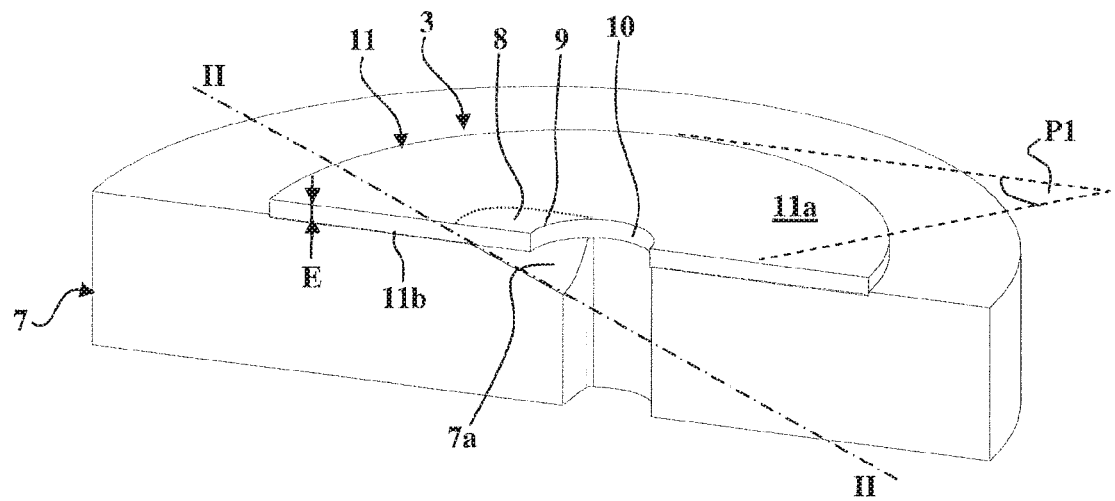
FIGS. 6 to 8 are perspective and cross-sectional views of the second workstation on which a flat metal blank is stamped to form a tooth.

In the production of the reamer 1 of FIG. 1, until the step of forming of the tooth 4, the cutter body 2 takes the form of a flat metal blank 11 partially illustrated in FIG. 6. This flat metal blank 11 is provided with a hole 10 with orifice 3. This hole 10 is preferably produced on a preceding workstation of the follow-on tool, and on which the blank 11 is cut by punching. The hole 10 defines the plane P1, which coincides here with the plane of the top face 11a of the flat metal blank 11.

The flat metal blank 11 has a thickness E of between approximately 0.4 mm and approximately 1 mm. The flat metal blank 11 is made of 304 L or 316 L grade stainless steel.

In FIG. 6, the blank 11 rests bearing on the anvil 7 by a face 11b. A portion 8 of wall 3 extends radially from and away from the hole 9 formed in the wall 3, and is situated to correspond with the pressing surface 7a of the anvil 7.

Figure 7:
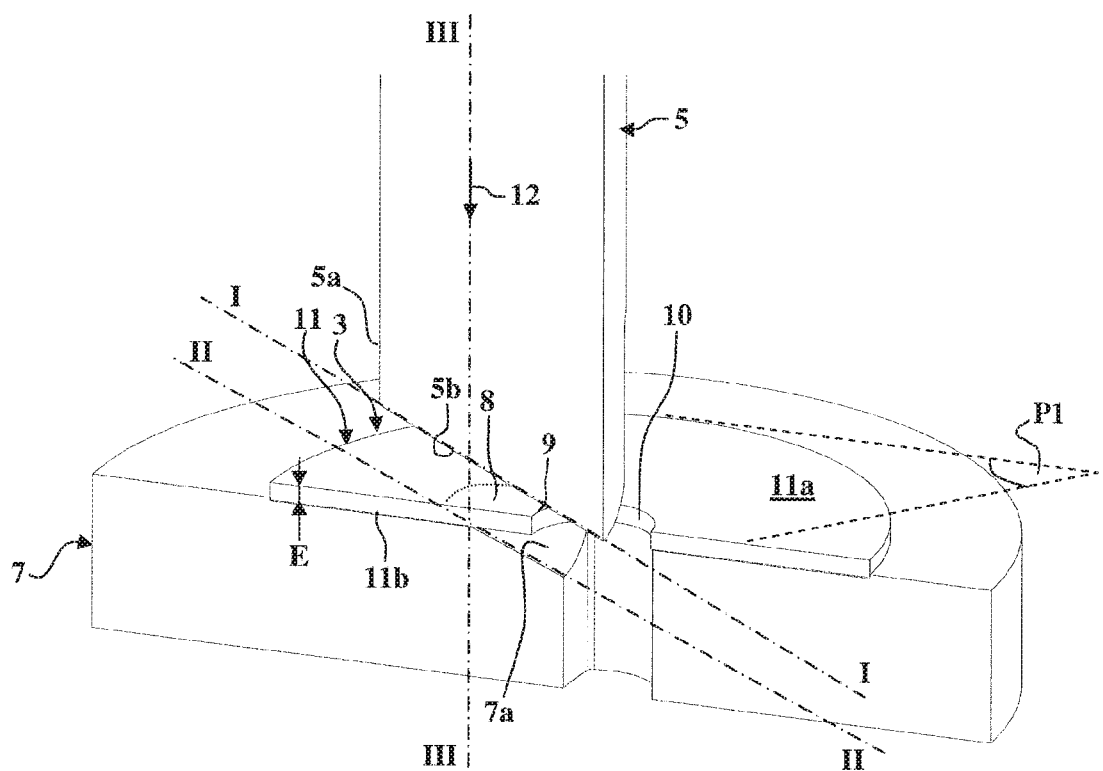

In a subsequent step, illustrated in FIG. 7, the punch 5 is displaced toward the anvil 7 (as illustrated by the arrow 12) in an axial direction III-III substantially at right angles to the plane P1.

Figure 8:
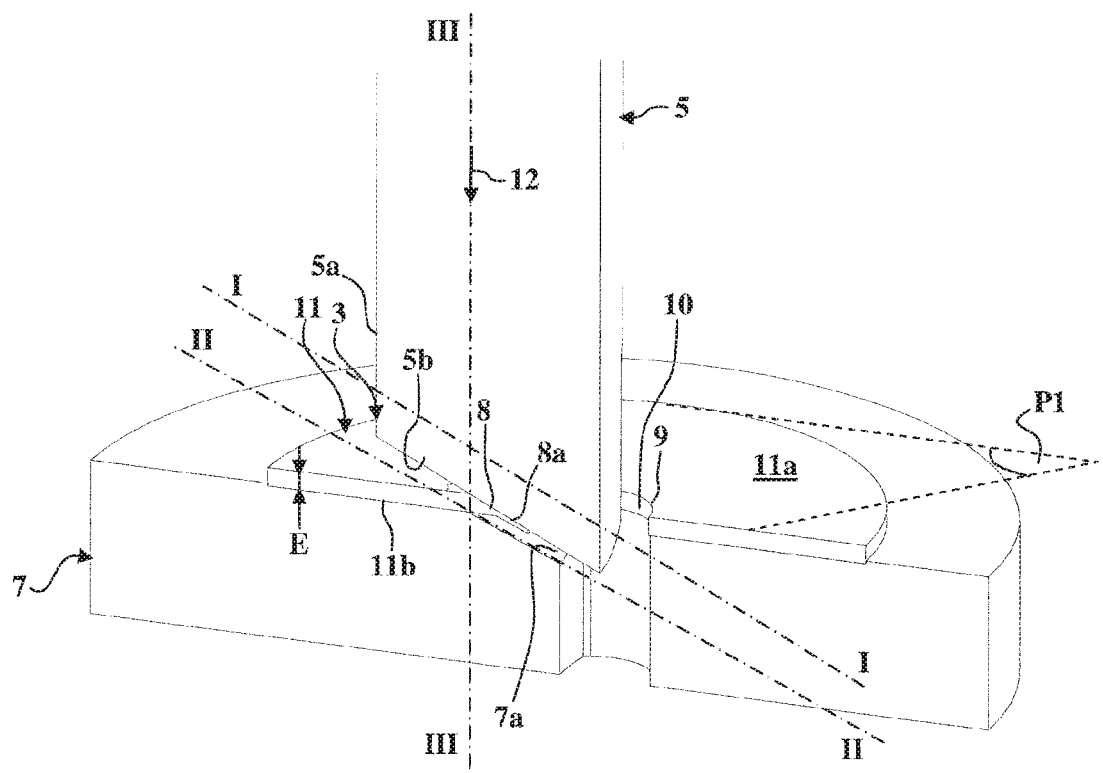

In this displacement, the punch 5 plastically deforms the portion 8 of wall 3 as illustrated in FIG. 8. Through the principle of conservation of material, a zone 8a of the deformed portion 8 of wall 3, adjacent to the hole 10, undergoes a thinning by virtue of its protruding displacement relative to the face 11b of the flat blank 11.

At the end of a certain travel of the punch 5, the zone 8a of deformed portion 8 of wall 3, adjacent to the hole 10, is pressed by the punch 5 against the anvil 7 (FIG. 9).

The stamping and the subsequent pressing between the punch 5 and the anvil 7 of the zone 8a of the deformed portion 8 of wall 3 provide a stretching and a thinning of the wall 3 to form the tooth 4. This thinning gives cutting capabilities to the free edge 4a of the duly formed tooth 4. By suitably controlling the pressing force, a thinning is achieved that is well controlled and repeatable for cutting characteristics that are substantially identical for all the teeth 4.

The pinching between the punch 5 and the anvil 7 provides a kind of local cold working of the tooth 4 (or fiber orientation of the material) which gives it an increased structural strength and a better durability over time during the use of the reamer 1.

Here, all of the portion 8 of wall 3 is pinched between the pressing surface 5b of the punch 5 and the pressing surface 7a of the anvil 7. It would however be possible to pinch only a part of the portion 8, said part extending from the hole 10 to at least form the free edge 4a of the tooth 4 by giving if cutting properties and a structural strength that are satisfactory.

It can be seen in FIG. 9 that, by virtue of the difference between the angles A1 and A2, the thickness of the portion 8 forming the tooth 4 increases progressively away from the free edge 4a of the tooth 4.

The punch 5 is then displaced away from the anvil 7 by a movement that is the reverse of that illustrated by the arrow 12 in FIG. 7. The blank 11 is then in the configuration illustrated in FIG. 10, and is then removed from the anvil 7 by means of ejectors.

Figure 11:
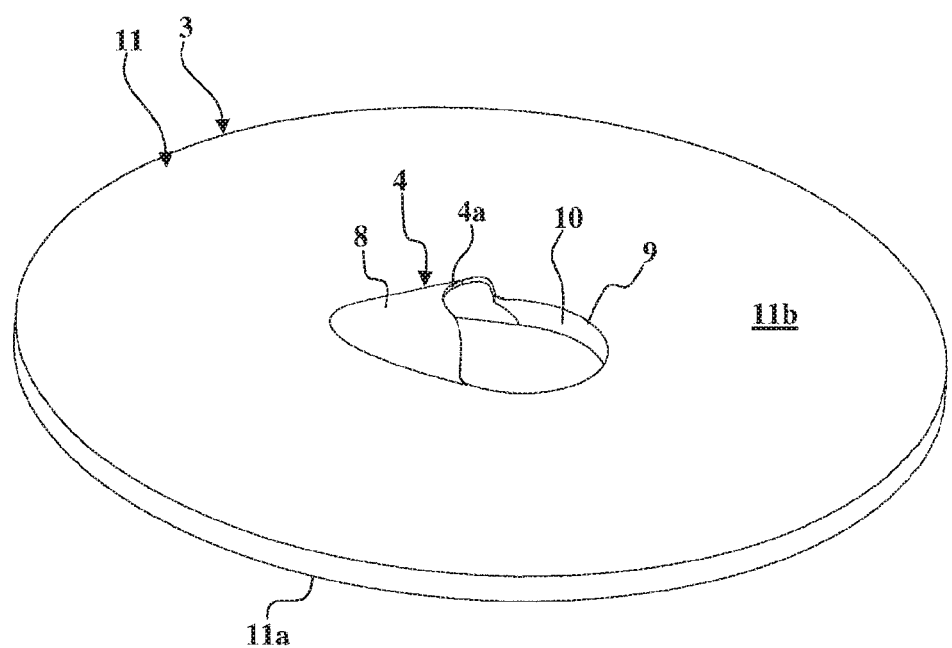
FIG. 11 is a perspective view of the metal blank after stamping to form a tooth.
Figure 12:
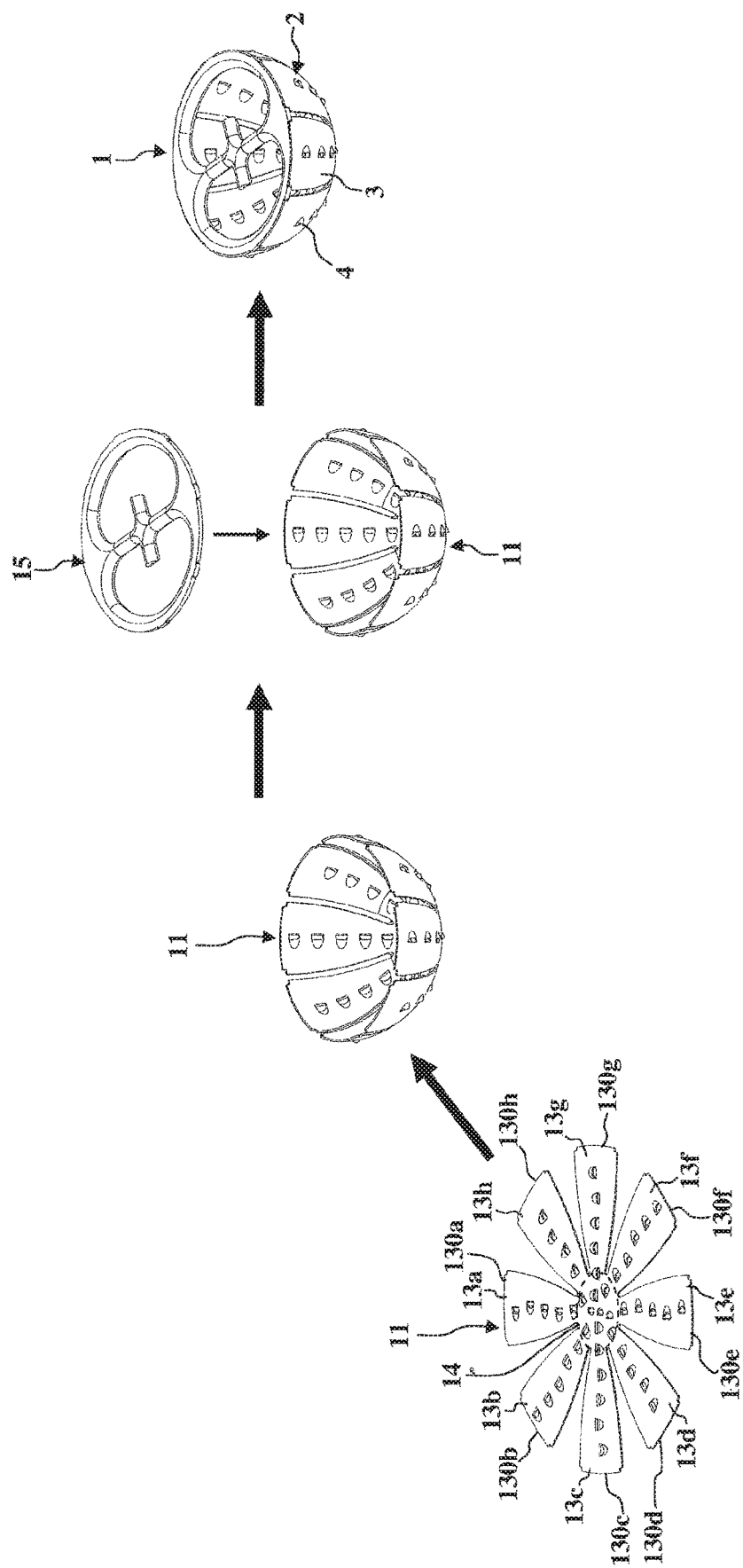
FIG. 12 is a schematic and perspective view illustrating a method for producing the reamer of FIG. 1.

FIG. 11 partially illustrates the blank 11 provided with the tooth 4 which forms a protuberance on the face 11b.

Once all the teeth 4 are formed in the flat metal blank 11, the latter is cut to obtain a plurality of perforated and toothed petals 13a to 13h extending radially from a central zone 14 from which the petals 13a to 13h extend to a free edge 130a to 130h. The petals 13a to 13h are separated from, one another by radial lateral, spaces (step a) in FIG. 12).

Next, in a step b), the flat blank 11 is shaped as a hemisphere. Then, in a step c), the free ends 130a to 130h of the petals 13a to 13h are added and fixed onto an at least partially circular base body 15. The blank 11 is then kept in substantially hemispherical dome form to form a cutter body 2 capable of milling the acetabular cavity of a patient.

The present invention is not limited to the embodiments which have been explicitly described, but it includes the miscellaneous variants and generalizations thereof contained in the scope of the claims hereinbelow.

The invention claimed is:

1. A method for producing a reamer, such as a milling cutter intended to mill the acetabular cavity of a patient, the milling cutter comprising a substantially hemispherical hollow cutter body with a perforated wall, said method comprising the steps of:
    a) providing a press comprising a stamp and an anvil;
    b) providing a flat metal blank designed to constitute the perforated wall;
    c) stamping a hole in the metal blank;
    d) forming at least one tooth by stamping the metal blank by means of a punch, and plastically deforming a portion of the metal blank extending radially from and away from the hole previously stamped in the wall;
    wherein:
    steps c) and d) are distinct, and wherein step d) is performed after step c);
    during step d), a zone of the deformed portion of the metal blank, adjacent to the hole, is plastically deformed, thinned, and pressed by the punch against the anvil to form a cutting edge.

2. The production method as claimed in claim 1, wherein: the punch comprises a free end with a set pressing surface, in the step of forming of the tooth, a generatrix (I-I) of the pressing surface is oblique relative to a plane (P1) defined by the orifice of the hole.

3. The production method as claimed in claim 2, wherein: the anvil comprises a set pressing surface whose generatrix (II-II) is oblique relative to the plane (P1) defined by the orifice of the hole,
    in the forming of the tooth, the angle (A2) between the generatrix (II-II) of the pressing surface of the anvil and the plane (P1) defined by the orifice of the hole is smaller than the angle (A1) between the generatrix (I-I) of the pressing surface of the punch and the plane (P1) defined by the orifice of the hole, preferably by approximately 2 degrees.

4. The production method as claimed in claim 1, wherein the flat metal blank has a thickness (E) of between approximately 0.4 mm and approximately 1 mm.

5. The production method as claimed in claim 1, wherein, after the forming of the tooth, the flat blank is cut to obtain a plurality of perforated and toothed petals extending radially from a central zone from which the petals extend to a free end, and separated from one another by radial lateral spaces.

6. The production method as claimed in claim 5, wherein, after the cutting of the flat blank to form the petals:
    the flat blank is shaped as a hemisphere,
    the free ends of the petals are added and fixed onto an at least partially circular base body.

7. The production method as claimed in claim 1, wherein the cutter body is made of stainless steel, preferably of 304 L or 316 L grade stainless steel.

* * * * *